United States Patent [19]
Dory

[11] Patent Number: 5,080,101
[45] Date of Patent: Jan. 14, 1992

[54] METHOD FOR EXAMINING AND AIMING TREATMENT WITH UNTRASOUND

[75] Inventor: Jacques Dory, Coupvray-Esblay, France

[73] Assignee: EDAP International, S.A., France

[21] Appl. No.: 368,906

[22] Filed: Jun. 19, 1989

Related U.S. Application Data

[60] Continuation of Ser. No. 37,369, Apr. 13, 1987, abandoned, which is a division of Ser. No. 728,905, Apr. 30, 1985, Pat. No. 4,658,828, which is a continuation-in-part of Ser. No. 674,889, Nov. 26, 1984, Pat. No. 4,617,931.

[30] Foreign Application Priority Data

Dec. 14, 1983 [FR] France .............................. 83 20041
May 3, 1984 [FR] France .............................. 84 06877

[51] Int. Cl.$^5$ ........................ A61B 8/00; A61N 5/00
[52] U.S. Cl. ............................... 128/660.03; 128/399
[58] Field of Search ................. 128/24 AA, 399, 804, 128/660.03

[56] References Cited

U.S. PATENT DOCUMENTS

| | | |
|---|---|---|
| 2,484,626 | 10/1949 | Keller . |
| 2,632,634 | 3/1953 | Williams . |
| 2,645,727 | 7/1953 | Willard . |
| 2,792,829 | 5/1957 | Calosi . |
| 3,168,659 | 2/1965 | Beyre et al. . |
| 3,237,623 | 3/1966 | Gordon .......................... 128/24 A |
| 3,338,235 | 8/1967 | Gordon .......................... 128/24 A |
| 3,560,913 | 2/1971 | Copley . |
| 3,735,755 | 5/1973 | Eggleton et al. .............. 128/24 A |
| 3,756,071 | 9/1973 | Dory . |
| 3,785,382 | 1/1974 | Schmidt-Kloiber et al. . |
| 3,810,174 | 5/1974 | Heard et al. . |
| 3,879,698 | 4/1975 | Pepper . |
| 3,911,730 | 10/1975 | Niklas . |
| 3,924,259 | 12/1975 | Butler et al. . |
| 3,927,557 | 12/1975 | Viertl . |
| 3,942,531 | 3/1976 | Hoff et al. . |
| 3,958,559 | 5/1976 | Glenn et al. .................. 128/24 A |
| 3,974,682 | 8/1976 | Soldner et al. . |
| 4,005,258 | 1/1977 | Dory . |
| 4,046,149 | 9/1977 | Kamiya . |
| 4,058,114 | 11/1977 | Soldner . |
| 4,070,905 | 1/1978 | Kossoff . |
| 4,084,582 | 4/1978 | Nigam . |
| 4,094,306 | 6/1978 | Kossoff . |
| 4,097,835 | 6/1978 | Green . |
| 4,163,394 | 8/1979 | Soldner . |
| 4,174,634 | 11/1979 | Dory . |
| 4,181,120 | 1/1980 | Kunii et al. . |
| 4,199,246 | 4/1980 | Muggli . |
| 4,204,435 | 5/1980 | Bridoux et al. . |
| 4,205,686 | 6/1980 | Harris et al. . |
| 4,209,022 | 6/1980 | Dory . |
| 4,218,768 | 8/1980 | Hassler . |
| 4,235,111 | 11/1980 | Hassler . |
| 4,245,511 | 1/1981 | Soldner . |
| 4,274,421 | 6/1981 | Dory . |
| 4,281,550 | 8/1981 | Erikson . |
| 4,281,661 | 8/1981 | Dory . |
| 4,287,770 | 9/1981 | Weyns . |
| 4,294,119 | 10/1981 | Soldner . |
| 4,305,296 | 12/1981 | Green et al. . |
| 4,311,147 | 1/1982 | Hausler . |
| 4,315,514 | 2/1982 | Drewes et al. ............... 128/660 X |
| 4,340,944 | 7/1982 | Dory . |
| 4,350,917 | 9/1982 | Lizzi et al. . |
| 4,368,410 | 1/1983 | Hance et al. . |
| 4,373,395 | 2/1983 | Borburgh et al. . |
| 4,375,818 | 3/1983 | Suwaki et al. . |
| 4,385,255 | 5/1983 | Yamaguchi et al. . |
| 4,412,316 | 10/1983 | Diepers . |

(List continued on next page.)

OTHER PUBLICATIONS

Cooper et al., "A Scanning, Focused Ultrasound ... ", Pro. 10th Ann NW Bio Eng Cond, Hanover, N.H., Mar. 1982, pp. 97-100.

(List continued on next page.)

*Primary Examiner*—Lee S. Cohen
*Attorney, Agent, or Firm*—William A. Drucker

[57] ABSTRACT

The disclosure relates to a method of ultrasonically locating and aiming treatment at a body target and displaying real time images of the body target. A treatment transducer produces a treatment beam of wave vibrations focused on said target and a separate scanning transducer displays images of said target on a display device during treatment with said beam together with a coincident image of a cursor which identifies the focal spot of the treatment beam.

41 Claims, 3 Drawing Sheets

U.S. PATENT DOCUMENTS

| | | | |
|---|---|---|---|
| 4,417,582 | 11/1983 | Trimmer et al. | |
| 4,434,341 | 2/1984 | Busby et al. | 128/804 X |
| 4,440,025 | 4/1984 | Hayakawa et al. | |
| 4,441,486 | 4/1984 | Pounds | 128/24 A |
| 4,458,533 | 7/1984 | Borburgh | |
| 4,462,092 | 7/1984 | Kawabuchi et al. | 367/105 |
| 4,470,308 | 9/1984 | Hayakawa et al. | |
| 4,474,180 | 10/1984 | Angulo | |
| 4,478,083 | 10/1984 | Hassler et al. | |
| 4,484,569 | 11/1984 | Driller et al. | |
| 4,486,680 | 12/1984 | Bonnet et al. | |
| 4,501,277 | 2/1985 | Hongo | |
| 4,526,168 | 7/1985 | Hassler et al. | 128/24 A |
| 4,535,771 | 8/1985 | Takayama | |
| 4,536,673 | 8/1985 | Forster | |
| 4,545,385 | 10/1985 | Pirschel | |
| 4,550,606 | 11/1985 | Drost | |
| 4,561,019 | 12/1985 | Lizzi et al. | |
| 4,564,980 | 1/1986 | Diepers | |
| 4,570,634 | 2/1986 | Wess | |
| 4,586,512 | 5/1986 | Do-huu et al. | |
| 4,608,983 | 9/1986 | Müller et al. | |
| 4,610,249 | 9/1986 | Makofski et al. | |
| 4,618,796 | 10/1986 | Riedlinger | |
| 4,618,887 | 10/1986 | Birk | |
| 4,620,545 | 11/1986 | Shene et al. | |
| 4,622,969 | 11/1986 | Forssmann et al. | |
| 4,622,972 | 11/1986 | Giebeler, Jr. | |
| 4,639,904 | 1/1987 | Riedlinger | |
| 4,646,756 | 3/1987 | Watmough et al. | |
| 4,671,292 | 6/1987 | Matzak | |
| 4,674,505 | 6/1987 | Pauli et al. | |
| 4,685,461 | 8/1987 | Forssmann et al. | |
| 4,721,106 | 1/1988 | Kurtze et al. | |
| 4,721,108 | 1/1988 | Heine et al. | |
| 4,858,597 | 8/1989 | Kurtze et al. | |

FOREIGN PATENT DOCUMENTS

| | | |
|---|---|---|
| 0000068 | 12/1978 | European Pat. Off. |
| 0036353 | 9/1981 | European Pat. Off. |
| 0045265 | 2/1982 | European Pat. Off. |
| 0068961 | 1/1983 | European Pat. Off. |
| 0072498 | 2/1983 | European Pat. Off. |
| 0081639 | 6/1983 | European Pat. Off. |
| 0090138 | 10/1983 | European Pat. Off. |
| 0108190 | 5/1984 | European Pat. Off. |
| 0124686 | 11/1984 | European Pat. Off. |
| 0133946 | 3/1985 | European Pat. Off. |
| 0155028 | 9/1985 | European Pat. Off. |
| 654673 | 12/1937 | Fed. Rep. of Germany |
| 2018468 | 10/1970 | Fed. Rep. of Germany |
| 2053982 | 5/1972 | Fed. Rep. of Germany |
| 2223319 | 12/1972 | Fed. Rep. of Germany |
| 2202989 | 7/1973 | Fed. Rep. of Germany |
| 2351247 | 4/1975 | Fed. Rep. of Germany |
| 2538960 | 4/1977 | Fed. Rep. of Germany |
| 2645738 | 4/1977 | Fed. Rep. of Germany |
| 2635635 | 2/1978 | Fed. Rep. of Germany |
| 2648908 | 5/1978 | Fed. Rep. of Germany |
| 2712341 | 5/1978 | Fed. Rep. of Germany |
| 2718847 | 11/1978 | Fed. Rep. of Germany |
| 2722252 | 11/1978 | Fed. Rep. of Germany |
| 2826828 | 7/1979 | Fed. Rep. of Germany |
| 2925933 | 3/1980 | Fed. Rep. of Germany |
| 2904115 | 8/1980 | Fed. Rep. of Germany |
| 2913251 | 10/1980 | Fed. Rep. of Germany |
| 2921444 | 11/1980 | Fed. Rep. of Germany |
| 3119295 | 12/1982 | Fed. Rep. of Germany |
| 3120611 | 12/1982 | Fed. Rep. of Germany |
| 3122056 | 12/1982 | Fed. Rep. of Germany |
| 3122056A1 | 12/1982 | Fed. Rep. of Germany |
| 3142639 | 5/1983 | Fed. Rep. of Germany |
| 3146626 | 6/1983 | Fed. Rep. of Germany |
| 3150513 | 6/1983 | Fed. Rep. of Germany |
| 3210919 | 10/1983 | Fed. Rep. of Germany |
| 3220751 | 12/1983 | Fed. Rep. of Germany |
| 3240691 | 4/1984 | Fed. Rep. of Germany |
| 3241026 | 5/1984 | Fed. Rep. of Germany |
| 3316837 | 11/1984 | Fed. Rep. of Germany |
| 3319871 | 12/1984 | Fed. Rep. of Germany |
| 3320998 | 12/1984 | Fed. Rep. of Germany |
| 3328068 | 2/1985 | Fed. Rep. of Germany |
| 3426398 | 3/1986 | Fed. Rep. of Germany |
| 1215631 | 4/1960 | France |
| 1334210 | 6/1963 | France |
| 2222658 | 10/1974 | France |
| 2247195 | 5/1975 | France |

OTHER PUBLICATIONS

Riedlinger et al., "Generating High-Energy Ultrasound . . . ", 3rd Congress of the Fed. of Acoust. Soc. Evr., Gottingen 1982.

Fry, "Precision High Intensity . . . Surgery", Am. J. Phys. Med., vol. 37, No. 3, Jun. 1978.

Berlinicke et al., "Uber Beeineflussung Von Gallensteinen Durch Ultraschall in Vitro", *Klinitsche Wochenschrift*, Dec. 28, 1950, p. 390.

Mulvaney, "Attempted Disintegration of Calculi by Ultrasonic Vibrations", *J. Urol.*, vol. 70, No. 5, Nov. 1953, pp. 704–707.

Bergmann, "Der Ultraschall—und Siene Anwendung in Wissen Schaft und Technik", S. Hirzel Verlag, Stuttgart, 1954, pp. 126–137.

Translation of 1938, pp. 1–39.

Coats, "Application of Ultrasonic Energy to Urinary and Biliary Calculi", *J. Urol.*, vol. 75, No. 5, May 1956, pp. 865–874.

Friedland, "Present Status of Ultrasound in Medicine", *The Journal of the American Medical Association*, vol. 163, No. 10, Mar. 1957, pp. 799–803.

Rozenberg, L. et al., "Apparatus for the Generation of Focused Ultrasound of High-Intensity", *Sov. Phys-Accoust.*, vol. 5, 1959, pp. 206–210.

Schlegel, J. et al., "The Use of Ultrasound for Localiz- (List continued on next page.)

OTHER PUBLICATIONS ing Renal Calculi", *J. Urol.*, vol. 86, No. 4, Oct., 1961, pp. 367-369.

Rosenberg, L. D., "La Generation Et L'Etude Des Vibrations Ultra-Sonores De Tres Grande Intensite", *Acustica*, vol. 12 (1962), pp. 40-49.

Rozenberg, L. et al., "A Focusing Radiator for the Generation of Superhigh Intensity Ultrasound at 1 Mc", *Sov. Phys-Acoust.*, vol. 9, No. 1, Jul.-Sep., 1963, pp. 47-50.

Gekhman et al., "The Effect of Supersonic Waves Upon the Kidneys and the Urinary Tract", (Russian) 1963, pp. 17-21.

Fry et al., "Ultrasonic Visualization of Soft Tissue Structure Based on Gradients in Absorption Characteristics", *The Journal of the Acoustical Society of America*, vol. 35, No. 11, Nov. 1963, pp. 1788-1790.

Eisenmenger, W., "Experimentelle Bestimmung der Stossfrontdicke aus dem Akustischen Frequenzspektrum Elecktromagnetisch Erzeugter Stosswellen in Flussigkeiten bei ein em Stossdruckbereich von 10 Atm bis 100 Atm", *Acustica*, (Publ. S. Hirzel Verlag, Stuttgart, Ger.), vol. 14, No. 4, 1964, pp. 187-204.

El'piner, I., *Ultrasound/Physical, Chemical, and Biological Effects*, 1964, (English translation by F. L. Sinclair, Consultants Bureau, N.Y.).

Frungel, F., *High Speed Pulse Technology*, vol. 1, Academic Press, 1965.

Tarnoczy, "Sound Focussing Lenses and Wave Guides", *Ultrasonics*, Jul.-Sep., 1965, pp. 115-127.

Thurstone, F. et al., "Resolution Enhancement in Scanning of Tissue", *Ultrasonics*, Jan. 1966, pp. 25-27.

Bulman, W., "Applications of the Hall Effect", *Solid-State Electronics*, vol. 9, 1966, pp. 361-372.

Lele, "Production of Deep Focal Lesions by Focused Ultrasound—Current Status", *Ultrasonics*, Apr. 1967, pp. 105-112.

Rozenberg, L., (Ed)., *Sources of High-Intensity Ultrasound*, vols. 1 and 2, 1969 (translations by James S. Wood, Plenum Press, N.Y.).

Fry, "Ultrasonic Visualization of Ultrasonically Produced Lesions in Brain," Confina Neurologica, vol. 32, pp. 38-52, 1970.

Rozenberg, L., (Ed), *High-Intensity Ultrasonic Fields*, 1971 (translation by James S. Wood, Plenum Press, N.Y.).

Hill, C. et al., "A Search for Chromosome Damage Following Exposure of Chinese Hamster Cells to High Intensity, Pulsed Ultrasound", *Brit J. Radiol.*, vol. 45, May, 1972, pp. 333-334.

*IEEE Transactions on Sonics and Ultrasonics*, Jan. 1973, p. 54.

Howards et al., "Current Status of Mechanical Lithotripsy", *Transactions of the American Association of Genito-Urinary Surgeons*, vol. 65, 1973, pp. 123-125.

Linke, C. et al., "Localized Tissue Destruction by High--Intensity Focused Ultrasound", *Arch. Surg.*, vol. 107, Dec. 1973, pp. 887-891.

Gavrilov, L. et al., "Use of Focused Ultrasound to Accelerate the 'Maturing' of a Cataract", *Sov. Phys-Acoust.*, vol. 20, No. 3, Nov.-Dec., 1974, pp. 229-231.

Greenleaf, J. et al., "Algebraic Reconstruction of Spatial Distribution of Acoustic Velocities in Tissue from their Time-of-Flight Profiles", *Acoustic Holography*, 1975, pp. 71-90.

Shaw, A. et al., "A Real Time 2-Dimensional Ultrasonic Scanner for Clinical Use", *Ultrasonics*, Jan., 1976, pp. 35-40.

Hill, C., "Ultra-Sonic Imaging", *J. Physics E Scientific Instruments*, vol. 9, Mar., 1976, pp. 153-162.

Sturtevant, B. et al., "The Focusing of Weak Shock Waves", *J. Fluid Mech.*, 1976, vol. 73, Part 4, pp. 651-671.

(List continued on next page.)

OTHER PUBLICATIONS

Wanner et al., "Problematik Einer Integrierten Ultraschallortung Im Versuchsmodell Beruhrungsfreie Nierensteinzertrummerung", Symposium Biophysikalische Verfahren Zur Diagnose und Therapie Von Steinleiden der Harnwege, Meersburg, Jun. 10 and 11, 1976, pp. 235-240.

Brinkmeyer et al., *Beobachtung Kurzer Kavitationsstosswellen mit Koharent-Optischen Methoden, DAGA '76, pp. 461-464.*

Portions of the 1977 Clinical Ultrasound Purchaser's Catalogue, (Publ. 1976 by McGraphics, Denver, Colo.).

Portions of the 1978 Clinical Ultrasound Purchaser's Catalogue, (Publ. 1977 by McGraphics, Denver, Colo.).

Wells, P. N. T., "Biomedical Ultrasonics", Academic Press, London, 1977, pp. 494-495.

Ibid., pp. 208-213.

Ibid., pp. 511-594.

Edell, S. et al., "Ultrasonic Evaluation of Renal Calculi", *Am J. Roentgenol*, 130:261-263, Feb. 1978.

Coleman et al., "Therapeutic Ultrasound in the Production of Ocular Lesions", *American Journal of Opthalmology*, 86:185-192, 1978.

Fry, "Ultrasound: Its Applications in Medicine and Biology", Elsevier Scientific Publishing Company, Amsterdam, 1978, pp. 689-707; 724-741; and 743-745.

Petersen, "Piezoelektrische Aktuatoren", Feinwerktechnik & Messtechnik, 86 (1978) pp. 304-308.

Raudsz, "Pschrometrische Bestimung", Feinwerktechnik & Messtechnik, 86 (1978).

Hausler et al., "Properties and Physiological Application of Focussed Fluid Shock Waves", ASA Meeting, Honolulu, Hi., Dec. 1978, pp. 2-12.

Kossoff, G., "Analysis of Focusing Action of Spherically Curved Transducers", *Ultrasound in Med. & Biol.* vol. 5, 1979, pp. 359-365.

Coleman, D. et al., "Experimental Investigations into Glaucoma Treatment Using High Intensity Focused Ultrasound", 24*th Annual Meeting of the American Institute of Ultrasound in Medicine*, Aug. 27-31, 1979, Paper No. 1301.

Fraatz, V. N. et al., "Lichtoptisch Abbildung Fokussierter Ultraschallfelder", *Materialpruf*, vol. 21, (1979) No. 10, Oct., pp. 359-363.

Konrad et al., "Fokussierte Stobwellen zur Beruhrungsfreien Nierensteinzertrummerung an der Freigelegten Niere", *Urologe A* 18 (1979), pp. 289-293.

von Klot, R., "Ausbreitung von Ultraschallimpulsen bei der Prufung von Kernreaktor-Druckbehaltern mittels Schallemissionsanalyse", *Materialpruf*, vol. 21 (1979), No. 10, Oct., pp. 353-358.

Romer, V. M. et al., "Fresnelsche Zonenplatte zur Schallfeldfokussierung", *Materialpruf*, vol. 21 (1979), No. 10, Oct., pp. 363-365.

Coleman et al., "Ultrasonically Accelerated Resorption of Vitreous Membranes", *American Journal of Opthalmology*, 89:490-499, 1980.

Wells, P. N. T., "Diagnostic Imaging in Europe", *Ultrasonics*, Mar., 1980, pp. 91-92.

"Echographie Ultrasonore: Un Circuit CCD Pour Simplifier L'Electronique De Commande", *Mesures Regulation Automatisme*—Fevrier 1980, pp. 25-27.

Lizzi et al., "Experimental Treatment of Intra-Ocular Carcinoma with High Intensity Focused Ultrasound", Paper No. 1305, Proceedings of the 25th Annual Meeting of the American Institute of Ultrasound in Medicine, Sep. 15-19, 1980, New Orleans, La.

Marshall, F. et al., "A Comparison of Ultrasonography and Radiography in the Localization of Renal Calculi: Experimental and Operative Experience", *J. Urol.*, vol. 126, Nov. 1981, pp. 576-580.

Hynynen, K. et al., "Design of Ultrasonic Transducers for Local Hyperthermia", *Ultrasound in Med. and Biol.*, vol. 7, No. 4, 1981, pp. 397-402.

Coleman, et al., "Applications of Therapeutic Ultrasound in Opthalmology", reprinted from Progress in Medical Ultrasound, vol. 2/1981, Amsterdam, Excerpts Medica, pp. 263-270.

Hausler and Stein, "Fokussierbare Unterwasserimpulsschallquellen", *Acustica*, vol. 49, No. 4, 1981, pp. 273-279.

Coleman et al., "Production of Alternate Filtration Paths for Treatment of Glaucoma with High Intensity Ultrasound", Paper No. 1303, AIUM/SDMS Annual Convention, San Francisco, Calif., Aug. 17-21, 1981.

Bulow et al., "Electrohydraulic Lithotripsy with Aspiration of the Fragments Under Vision—304 Consecutive Cases", *J. Urol.*, vol. 126, Oct. 1981, pp. 454-456.

Chaussy et al., "First Clinical Experience with Extracorporeally Induced Destruction of Kidney Stones by Shock Waves", *J. Urol.*, vol. 127, Mar. 1982, pp. 417-420.

*Ultrasonics*, May 1982, pp. 99-101.

(List continued on next page.)

OTHER PUBLICATIONS

Chaussy, "Beruhrungsfreie Nierensteinzertrummerrung Durch Extrakorporal Erzeugte, Fokussierte Stobwellen", *Beitrage Zur Urologic*, vol. 2, Karger, Basel, 1980, pp. 40-41, Translation of entire source included.

Chaussy et al., "Extracorporeal Shock Wave Lithotripsy—New Aspects in the Treatment of Kidney Stone Disease", Karger, Basel, 1982.

Ziegler et al., "Erfahrungen mit Hochenergetischen Stobwellen Bei der Behandlung Von Nierensteinen", Results of High Intensity Shock Wave Treatment of Renal Calculi, Program of the 7th Annual Meeting, European Intrarenal Surgery Club, Ghent, Belgium, 1982 (Translation included).

Program of the 7th Annual Meeting, European Intrarenal Surgery Club, Ghent, Belgium, 1982.

*Ultrasonics*, Jan. 1983, pp. 5-6.

Watanabe et al., "Micro-Explosion Cystolithotripsy", *J. Urol.*, vol. 129, Jan. 1983, pp. 23-28.

Campbell, J. et al., "Normalization of Ultrasonic Scattering Measurements to Obtain Average Differential Scattering Cross Sections for Tissues", *J. Acoust. Soc. Am.*, vol. 74, No. 2, Aug. 1983, pp. 393-399.

Hunt et al., "Ultrasound Transducers for Pulse-Echo Medial Imaging", IEEE Transactions on Biomedical Engineering, vol. BME-30, No. 8, Aug. 1983, pp. 453-481.

Hynynen et al., "A Clinical Hyperthermia Unit Utilizing an Array of Seven Focused Ultrasonic Transducers", 1983, Ultrasonics Symposium, IEEE, pp. 816-821.

Chaussy et al., "Shock Wave Treatment for Stones in the Upper Urinary Tract", *Urologic Clinics of North America*, vol. 10, No. 4, Nov. 1983, pp. 743-750.

Macovski, "Medical Imaging Systems", pp. 4-6 and 173-181, 1983, Prentice-Hall, Inc.

Brannen et al., "Ultrasonic Destruction of Kidney Stones", Original Clinical Articles, Mason Clinic, Seattle, Feb., 1984, vol. 140, No. 2, pp. 227-232.

Duck, F. et al., "Acoustic Shock Generation by Ultrasonic Imaging Equipment", *Brit. J. Radiol.*, Mar. 1984, pp. 231-240.

Chaussy et al., "Extracorporeal Shock Wave Lithotripsy (ESWL) for Treatment of Urolithiasis", Special Issue to *Urology*, vol. 23, No. 5, May 1984, pp. 59-66.

Elder et al., "Ultrasonic Lithotripsy of a Large Staghorn Calculus", *J. Urol.*, vol. 131, Jun. 1984, pp. 1152-1154.

Lizzi, F., "Ultrasonic Hyperthermia for Ophthalmic Therapy", *IEEE Transactions on Sonics and Ultrasonics*, vol. SU-31, No. 5, Sep. 1984, pp. 473-481.

Lizzi, et al., "Thermal Model for Ultrasonic Tretment of Glaucoma", *Ultrasound in Med. & Biol.*, vol. 10, No. 3, 1984, pp. 289-298.

Chaussy et al., "Extrakorporale Stobwellenlithotripsie—Beginn einer Umstrukturierung in der Behandlung des Harnsteinleidens?", *Urologe A*, vol. 23, 1984, pp. 25-29.

Chaussy, et al., "Extracorporeal Shock Wave Lithotripsy for the Treatment of Urinary Tract Stones", *Hospimedica*, Sep.-Oct. 1986, pp. 21-27.

"Ultrasonic Focusing Radiators", pp. 225-285, 306-307.

Kurtze, "Uber die Bedingunguen fur das Auftreten von Kavitation in Flussigkeiten", (source unknown), pp. 1-47.

Bittner, "Uber Die Moglichkeiten, Nierensteine Mit Hilfe Des Ultraschall-A-Verfahrens Nachzuweisen Und Zu Lokalisieren", *Symposium/Biophysikalische Verfahren zur Diagnose und Therapie von Steinleiden der Harnevege Wissenschaftliche Berichte*, Meersburg, Jun. 10-11, 1976, pp. 61-69.

Bartels, "Zur Frage Der Nierenstein-Darstellung Mit Der B-Scan Sonographie", *Symposium/Biophysikalische Verfahren zur Diagnose und Therapie von Steinleiden der Harnevege Wissenschaftliche Berichte*, Meersburg, Jun. 10-11, 1976, pp. 70-73.

Bartels, "Intraoperative Rontegenunterschungen Der Niere Mit Dem Renodorgerat", *Symposium/Biophysikalische Verfahren zur Diagnose und Therapie von Steinleiden der Harnevege Wissenschaftliche Berichte*, Meersburg, Jun. 10-11, 1976, pp. 74-81.

Guilgkett, "Stobspannungen und Stobstrome" (Symp.e unknown), pp. 2-22.

Hausler, "Physikalische Grundlagen Der Instrumentellen Under Der Extrakorporalen Zerkleinerung Von Harnsteinen", *Symposium/Biophysikalische Verfahren zur Diagnose und Therapie von Steinleiden der Harnevege Wissenschaftliche Berichte*, Meersburg, Jun. 10-11, 1976, p. 32.

Hausler et al., "Ultraschallverfahren Zur Ortung Von Nierensteinen", *Symposium/Biophysikalische Verfahren zur Diagnose und Therapie von Steinleiden der Harnevege Wissenschaftliche Berichte*, Meersburg, Jun. 10-11, 1976, pp. 54-60.

(List continued on next page.)

OTHER PUBLICATIONS

Lauterborn, Session 3, "Cavitation: General and Basic Aspects", 3:1—General and Basic Aspects of Cavitation, pp. 195-202.

Wells, P. N. T., "Ultraschall in der Medizinischen Diagnostik", Walter de Gruyter, Berlin, 1980.

Wells, P. N. T., "Scientific Basis of Medical Imaging", Churchill Livingstone, Edinburgh, 1982.

*Symposium/Biophysikalische Verfahren zur Diagnose und Therapie von Steinleiden der Harnevege Wissenschaftliche Berichte,* Meersburg, Jun. 10-11, 1976.

Hepp, W., *Uberblick uber die Entwicklung der Stosswellenlithotripsie,* (Publ. Dornier Medizintechnik), Sep. 1984.

Programme and Abstract, BMUS 13th Annual Meeting, 14th-15th Dec. 1981, London.

Sources of High Intensity Ultrasound, Rozenberg, vol. 1, Plenum Press, N.Y., 1969—Article entitled "Ultrasonic Focusing Radiators", pp. 288-305.

Progress in Medical Ultrasound, vol. 2—1981, Edited by Kurjak—"Applications of Therapeutic Ultrasound In Ophthalmology", Coleman, Lizzi, Chang & Driller, pp. 263 to 270.

Ultrasound: Its Applications in Medicine and Biology, vol. 3, Part II, Edited by Fry, 1978, Chap. 14, pp. 689-707.

*American J. of Ophthalmology,* vol. 86, No. 2, 8-78, "Therapeutic Ultrasound in the Production of Ocular Lesions", Coleman, Lizzi & Jakobiec, pp. 185-192.

*Ultrasonics,* Apr. 1967, pp. 105-112, Article by Lele, "Production of Deep Focal Lesions".

METHOD FOR EXAMINING AND AIMING TREATMENT WITH UNTRASOUND

CROSS REFERENCE TO PRIOR APPLICATIONS

This is a continuation of Ser. No. 037,369, filed Apr. 13, 1987, abandoned, which is a division of Ser. No. 728,905, filed Apr. 30, 1985, which is U.S. Pat. No. 4,658,828, now Reissue No. 33,590 of May 21, 1991 which is a continuation-in-part of Ser. No. 674,889, filed Nov. 26, 1984, now U.S. Pat. No. 4,617,931, now Re-Examination Certificate B1-4,617,931 of July 12, 1988.

BACKGROUND OF THE INVENTION

Conventional echography apparatus are used for examining tumors inside the body by forming an image thereof on the screen of a cathode ray tube.

As is known, it is also possible to obtain destruction of the cells—particularly malignant cells—by subjecting them to extended temperature rise. The cells to be destroyed must, for example, be brought to about 45 degrees C. in a well controlled way while avoiding reaching excessive temperatures which could cause serious burns around the lesion. One of the technical problems to be resolved for hyperthermia and other treatment applications consists both in controlling the amount of energy and the localization thereof.

With different prior art processes (use of ultrahigh frequencies, infrared radiation and others) superficial tumors can be treated but deeper tissues cannot be reached.

The invention proposes applying ultrasound to examination processes used in hyperthermia and other treatment and provides a method and apparatus which combines the three functions of localizing the zone to be treated, of treating in a well controlled way in a well defined restricted region within this zone and simultaneously checking the results of the treatment during treatment.

SUMMARY OF THE INVENTION

The method and apparatus of the invention can be used for hyperthermia and other kinds of treatment. The method and apparatus of the invention combines a generator exciting a pulsed focused treatment beam comprising a main high frequency wave emitter and a main transducer, with a separate echography device comprising an auxiliary high frequency pulse generator associated with an auxiliary piezoelectric transducer and with means for causing the zone to be treated to be swept during treatment by the ultrasonic examination beam generated by the auxiliary transducer. The invention includes switching and adjusting means for causing, during main power treatment and checking operations, the pulsed emission of a treatment sequence of vibration discharges as a focused beam by the main transducer, energized by the main emitter, during periodic time intervals.

The invention advantageously comprises a first auxiliary locating operation mode during which the emission of the examination beam as scanning pulses by the auxiliary transducer is effected; and preferably a second auxiliary operating mode for checking the focal region, during which only the periodic emission of the treatment beam is effected. The main emitter preferably is synchronized by the synchronization circuit of the auxiliary generator for echographic operation for hyperthermia treatment, the time intervals which separate the successive emission periods during the two auxiliary operating modes being substantially smaller then the intervals which separate the periods of emission of the focused beam during the treatment mode.

During the auxiliary operating modes for obtaining accurate adjustments, the quality of the echographic image, either of the zone located within a body to be treated (locating mode) or of the focal region (mode for checking the restricted region), will be substantially better than during the treatment mode, during which the successive images of the zone to be treated in the case of hyperthermia treatment will follow each other for example at intervals of the order of a second, which however allows the position of the focal region to be checked satisfactorily during treatment.

In a preferred embodiment, the auxiliary transducer is connected to the main transducer which comprises a concave focusing surface and thus, during movement of the treatment transducer to bring the focal spot into successive restricted regions of the zone, the auxiliary transducer will at all times supply an image of the treated region and of the zone which surrounds it, thus allowing a continuous check of the treatment zone to be effected easily and accurately.

BRIEF DESCRIPTION OF THE DRAWINGS

Other features and advantages of the invention will be clear from the following description.

In the accompanying drawings.

DESCRIPTION OF THE PREFERRED EMBODIMENT

Figure 2:
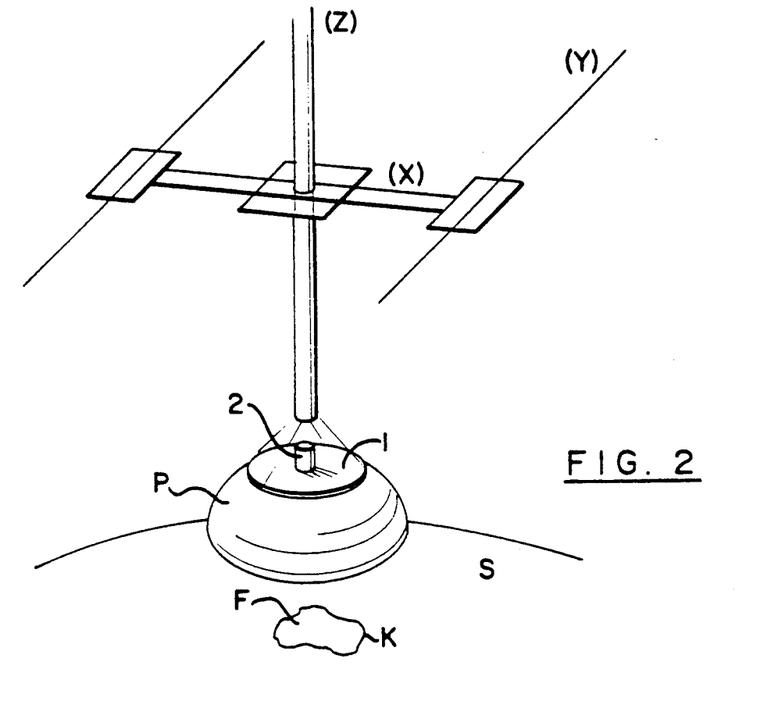
FIG. 2 shows schematically in perspective the main transducer and its mobile support device.

In FIG. 2 is shown a main treatment transducer 1 in the form of a spherical skull cap supported by a mount which allows it to move, in any order, along three orthogonal axes X, Y and Z. This mount has been shown schematically, its construction being within the scope of a man skilled in the art. Generally along or in the direction of any axis of the spherical skull cap there is disposed an auxiliary transducer 2 of a generally cylindrical shape which preferably passes through skull cap 1 and is connected thereto. A pocket of water P is placed between the skull cap 1 and a patient so that the pocket wall contacts the surface S of the body of the patient, who is assumed to be lying flat on a horizontal plane to provide an acoustic coupling through a portion of the body.

Figure 1:
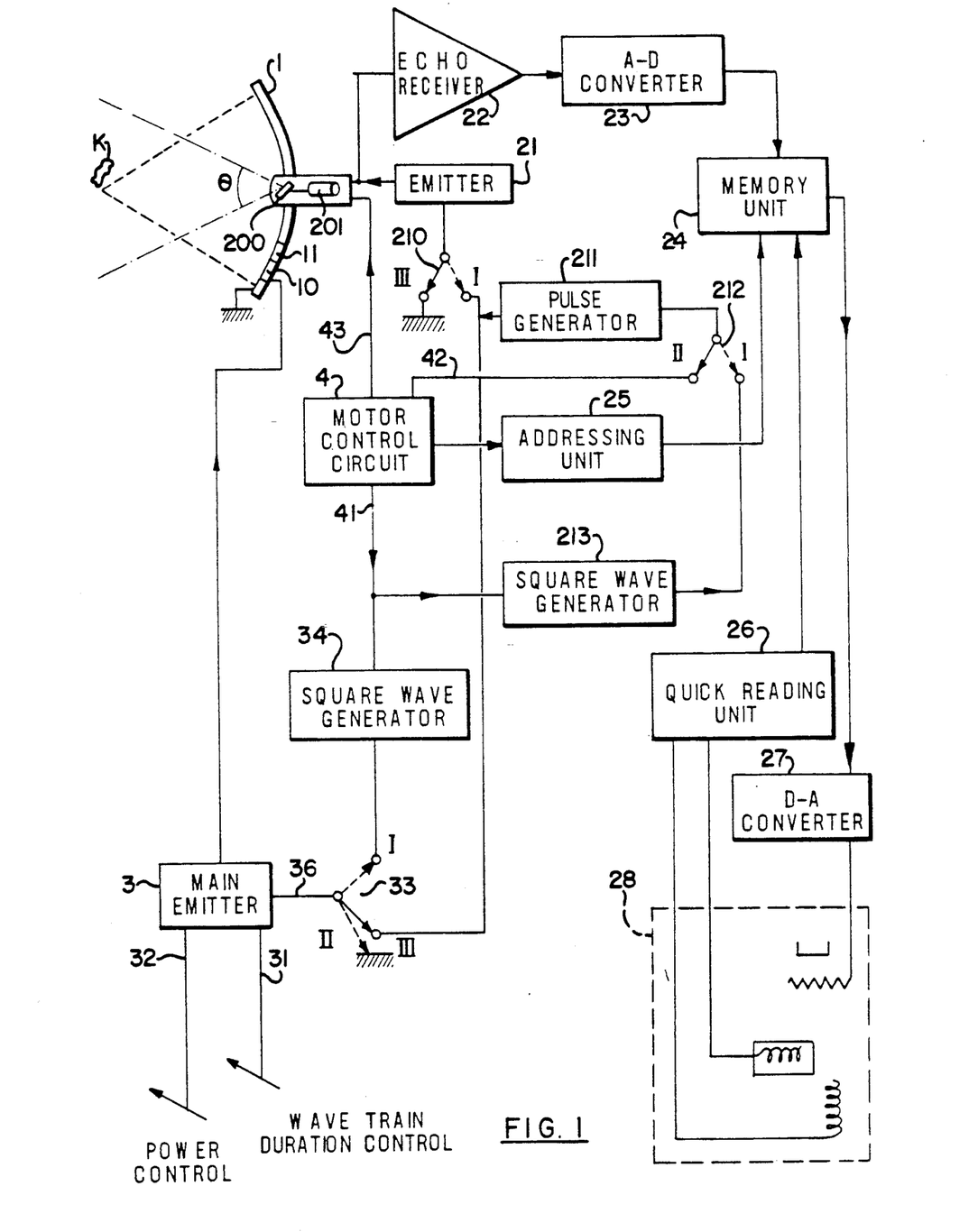
FIG. 1 is a general diagram of a hyperthmia apparatus used according to a preferred embodiment of the invention.

The skull cap 1 has for example a diameter of 200 to 300 mm and when it is an active surface is formed from a large number (300 or 400) of piezoelectric elements 10, 11, etc. . . . (FIG. 1) isolated from each other and juxtaposed to form a mosaic. The elements are metallized on both faces, one of the metallizations being connected to ground and the other to connections for energization by a main emitter 3 (FIG. 1).

Emitter 3 delivers an interrupted electric signal to form high frequency waves (500 KHz for example) in a treatment sequence as pulsed vibration discharges separated by interruption time intervals of the order of 1/10 second, the time required for the echography device to form an image. Operating conditions may be obtained by means of emitters using power transistors.

Preferably, the elements of transducer 1 will be divided up into groups each energized by a separate emitter (rectangle 3 symbolizing the assembly of these emitters), the elements of each group being spaced apart in the same circular zone of the spherical surface. By adjusting the relative phases of the emissions, it is possible to modify the energy distribution in the focusing region of the treatment beam.

An input 31 to emitter 3 symbolizes means for adjustment of the emitted power and an input 32 symbolizes means for adjustment of the pulse shape or treatment wave duration. The focal spot formed in the center F of the sphere may, with this technique, be very small (diameter of 2 or 3 mm for example) and have a position which is strictly fixed for a given position of the transducer.

In FIG. 1 it can be seen that the auxiliary transducer 2, which may comprise an active surface, is itself connected both to a separate high frequency electric pulse emitter 21 and to a reception amplifier 22 followed by an analog-digital converter 23, itself followed by a memory 24. Emitter 21 can be connected to and synchronized by a pulse generator 211 which delivers a sequence of 256 pulses during each of the successive time intervals of 1/10 second. An acoustic signal beam is radiated and swept across the zone. Each of these time intervals corresponds a complete sweep of a given angular sector theta (FIG. 1) by the beam emitted by transducer 2.

Transducer 2 is advantageously of the type described in U.S. Pat. No. 4,418,698, granted on Dec. 31, 1983, comprising an oscillating piezoelectric element 200 controlled by a motor 201, itself controlled by an electronic circuit which is shown symbolically by a rectangle 4. This circuit provides control signals for the motor 201 housed inside the case of the transducer 2 and is adapted so that a complete oscillation of the motor corresponds to the above defined duration for forming an image (1/10 second).

In a first operating mode (treatment and checking) switch 210 is in a position I as well as switches 212 and 33. In position I of switches 33 and 212, generator 211 is synchronized by a first output 41 of circuit 4, which is adjusted, by means not shown, for generating signals at its output 43 connected to motor 201. An image is then swept through the water pocket in 1/10 second in which the echoes are converted to displayed electric signals and is followed by a time interval of one second during which transducer 2 receives no echoes.

During intervals between the sweep periods, a circuit 34 generates square waves of one second which synchronize emitter 3, whereas, during the sweep periods, a circuit 213 generates square waves of 1/10 second which synchronize the generator 211.

Thus, in this operating mode, transducer 1 generates an interrupted treatment beam under substantially continuous operating conditions as a treatment sequence whereas the echography device forms an image every second in the interruptions or intervals between the waves. The wave forms of the signals emitted by generator 211 are shown at Bt.

In a second operating mode (locating) with switch 210 in position I, switch 33 is in position II, so that emitter 3 is not synchronized and the focused ultrasonic treatment beam is not emitted. Switch 212 is also in position II so that generator 211 is synchronized by a second output 42 of circuit 4 which is adjusted to generate signals at its output 43. The 1/10 second echography sweeps are separated by intervals of only 1/100 second and the images are formed from echoes converted to electric signals coming from reflection of the pulses generated by transducer 2. Generator 211 delivers the signals.

In a third operating mode (checking the focal region), switch 210 is in position III, so that the emitter 21 and transducer 2 do not emit. Switch 212 is again in position II so that generator 211 is synchronized by the output 42 of circuit 4 which is adjusted as in the second operating mode so that the 1/10 second sweeps are again separated by intervals of 1/100 second. Switch 33 is in position III and consequently emitter 3 is synchronized by the generator 211 which then delivers the signals. In this third operating mode, the echographic device is therefore formed by emitter 3, transducer 1 operating for emission and transducer 2 operating for reception. The result is that an image of the distribution of the concentration of energy in the focal region emitted by the transducer 1 is obtained.

The echographic signals from the reflected surfaces in the treated zone received at 22 in the first or third operating modes are, after analog-digital conversion at 23, stored line by line in memory 24, a writing addressing device 25, controlled by circuit 4, causing the respective deflection angles of the beam emitted and/or received by transducer 2 to correspond with the respective lines of the memory. A device 26 for rapid reading of the memory energizes the X and Y deflection coils of a cathode ray tube 28, so the brightness control electrode receives the corresponding contents from memory 24, transformed into an analog signal by a digital-analog converter 27. The electrical signals are then displayed as an image of the anomaly in the zone.

The practical construction of all the circuits described and shown is within the scope of a man skilled in the art. The control circuit 4 may for example comprise a one shot multivibrator delivering square waves of a duration adjustable to 1/100 second or one second depending on the operating mode and circuits for generating increasing and decreasing voltages of a 1/10 second duration, triggered by said square waves.

Figure 3:
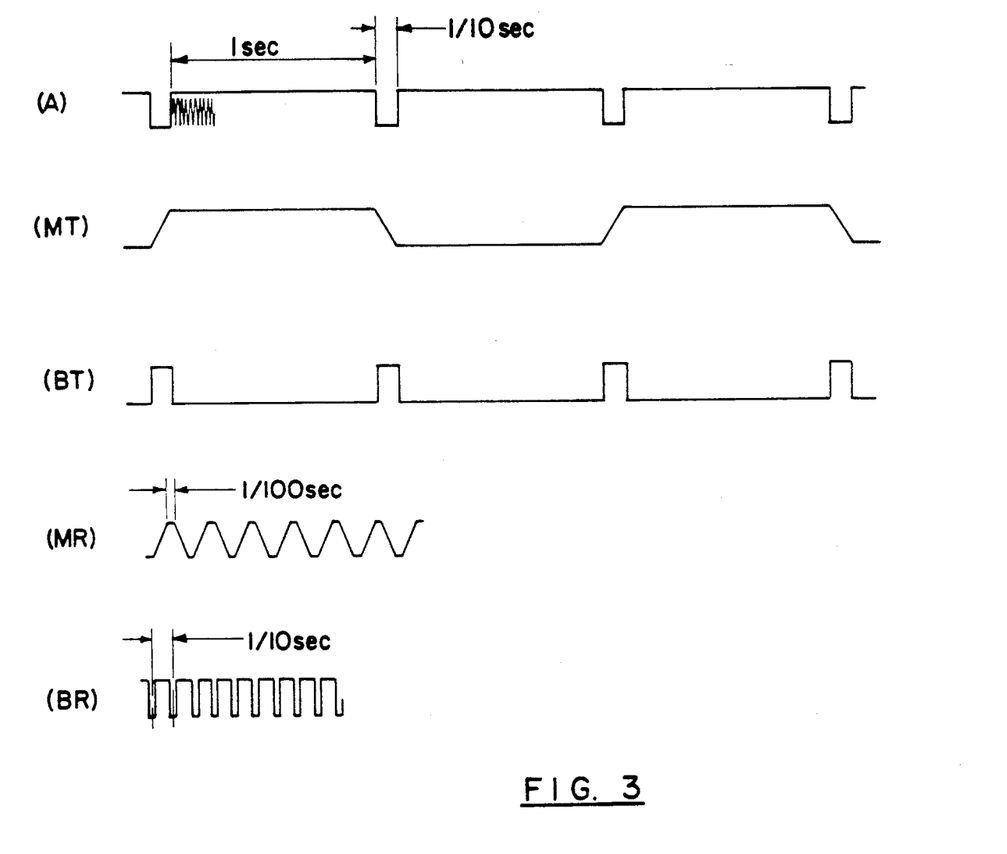
FIG. 3 shows the wave forms for hyperthermia treatment at different points of the circuit of the apparatus.
Figure 4:
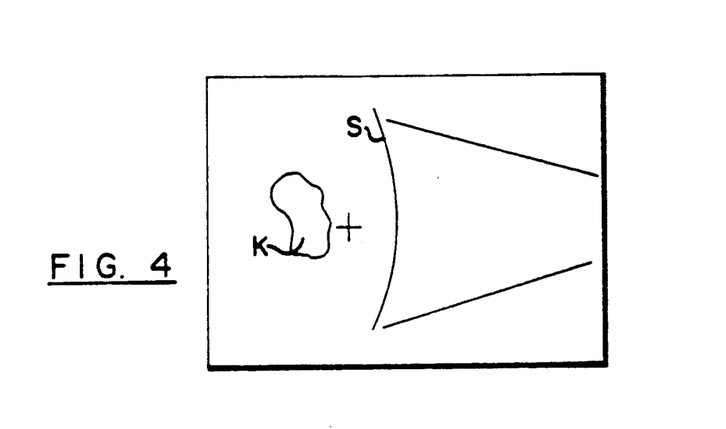
FIG. 4 illustrates the image obtained on the display screen according to the method described.

The apparatus and method which has just been described operates as follows:

In the locating operating mode, the operator searches for and localizes the zone to be treated and/or altered. The display device is adapted, in a way known per se, so as to materialize a cursor mark on the screen of a cathode ray tube (for example by a cross) indicating the theoretical position of the focal spot in the sectional plane shown, which plane passes through the axis of symmetry of transducer 1. The mark and zone are then maintained in coincidence. (It is a matter of B type echography). The operator begins aiming by moving transducer 1 in any order, for example first along axis X, until the treatment zone appears clearly on the screen, then he moves it along axes Y and Z, until the cursor cross mark coincides with the central region of the image of the zone (K, FIG. 3). At this moment, the switches may be placed in position for checking the focal region: only this latter is then visible on the screen, with a luminosity proportional to the corresponding distribution of energy concentration. Thus a representation is obtained of what the distribution of the energy of the treatment wave will be during treatment, which allows the adjustments to be checked and perfected.

During treatment, the apparatus and method supplies only one image per second, but this rate is sufficient for substantially continuously checking the position of the focal spot.

It is clear that the method described allows the evolution of the treatment to be checked both during and after each treatment sequence. It is evident that different modifications may be made thereto and even according to other embodiments, without departing from the scope and spirit of the invention.

I claim:

1. A method for examining, localizing and treating a zone within a body comprising the steps of:
    (a) generating a first treatment beam from a first transducer focused on said zone;
    (b) successively discharging said first beam to treat said zone with said first beam;
    (c) generating a second imaging scanning beam from a separate second transducer;
    (d) effecting a scanning of said zone with said second beam within the path of the treatment beam by sweeping said second beam across said zone to effect imaging of said zone;
    (e) receiving the echoes formed through reflection of said second beam on reflecting surfaces of said zone and converting said echoes into electrical signals; and displaying said signals during treatment at least between successive treatment discharges as serial real time images; further including:
    (f) exciting treatment vibrations with said first beam, in treatment discharges which are separated by time intervals, to form a treatment sequence of discharges;
    (g) effecting the separate generation of imaging scanning pulses with said second beam during at least said intervals in said treatment sequence to form images of said zone by sweeping said second beam through water across an angular sector containing said zone; and
    (h) effecting and maintaining coincidence of said images with a mark which indicates during treatment the position of a focal point of said treatment beam.

2. A method as set forth in claim 1 wherein said treatment is for effecting hyperthermia by causing local heating at the treatment beam focus in said zone.

3. A method as set forth in claim 1 wherein said treatment beam is an ultrasonic beam.

4. A method as set forth in claim 1 wherein said treatment is for causing a therapeutic increase in the temperature of said zone by local heating at the focus of the treatment beam.

5. A method as set forth in claim 1 wherein said second beam is emitted within said path of said treatment beam.

6. A method for treating a body zone comprising the steps of:
    (a) generating an interrupted wave treatment beam having a focus from a first treatment beam generator;
    (b) treating said zone with said treatment beam;
    (c) generating a separate echography imaging scanning ultrasound beam from a second generator distinct from said first treatment generator;
    (d) effecting a scanning of said zone with said echography beam at least during interruptions of said treatment beam by sweeping said echography beam across said zone to effect imaging of said zone;
    (e) receiving echoes formed through reflection of said echography beam on said zone and converting said echoes into electrical signals to display images of said zone;
    (f) displaying real time images of said zone on a display device coincident with a cursor mark displayed on said device which indicates the position of said focus of said treatment beam; and
    (g) maintaining said images of said zone in coincidence with said cursor mark while scanning said zone with said echography beam.

7. A method according to claim 6 in which said treatment beam is displaced to bring said mark into coincidence with said real time images.

8. A method as set forth in claim 6 wherein said treatment is for effecting hyperthermia by causing local heating at the treatment beam focus in said zone.

9. A method as set forth in claim 6 wherein said treatment beam is an ultrasonic beam.

10. A method as set forth in claim 6 wherein said treatment is for causing a therapeutic increase in the temperature of said zone by local heating at the focus of the treatment beam.

11. A method as set forth in claim 6 wherein the step of generating an interrupted treatment beam comprises generating groups of treatment waves, each group having a duration during which treatment waves are emitted from said first treatment beam generator, said groups of treatment waves being separated by said interruptions during which no treatment waves are emitted, each of said interruptions having a duration, said duration of each of said groups of treatment waves being longer in time than the duration of each of said interruptions.

12. A method as set forth in claim 6 wherein the step of generating an interrupted wave treatment beam comprises generating from said first treatment beam generator groups of treatment waves separated by said interruption during which no treatment waves are generated, each of said groups of treatment waves comprising at least two treatment waves.

13. A method of treating a zone within a body by focused discharges of treatment vibrations, comprising the steps of:
    (a) identifying and locating said zone within said body by ultrasound echography scanning using an ultrasound beam source and displaying an image of said zone on an image display device;
    (b) generating a treatment beam of vibrations from a second beam source directed at a focus and focusing said treatment beam onto said zone by bringing and maintaining a cursor mark on said display device, indicating said focus of said treatment beam, into coincidence with said ultrasound image of said zone;
    (c) treating said zone with said vibrations from said second source by transmitting said vibrations through water; and
    (d) providing a real time echographic image display of said zone by sweeping and scanning ultrasound waves from said first source through said water to check said zone location and treatment progress at least between treatment pulses during treatment of said zone.

14. A method as set forth in claim 13 wherein said treatment is for effecting hyperthermia by causing local heating at the treatment beam focus in said zone.

15. A method as set forth in claim 13 wherein said treatment beam is an ultrasonic beam.

16. A method as set forth in claim 13 wherein said treatment is for causing a therapeutic increase in the temperature of said zone by local heating at the focus of the treatment beam.

17. A method for treating a zone, having a least one reflecting surface for ultrasonic waves and located within a body, by treatment vibrations, said method comprising the steps of:
 (a) locating said zone by generating, from a first transducer means having an active surface a first real time scanning ultrasonic beam and sweeping said zone with said first beam, whereby echoes are formed through reflection of said first beam on said at least one reflecting surface; receiving said echoes upon said active surface; converting said received echoes into electric signals and forming from said signals two dimensional real time images of said zone through at least one plane;
 (b) providing from a second transducer means a focused treatment beam of treatment vibrations converging at a focal point which is located in said at least one plane and is indicated by display of a cursor mark;
 (c) displacing said focal point of said second transducer means relative to said zone and placing said mark of said focal point in registration with said images of said zone; and
 (d) thereafter treating said zone with treatment vibrations while observing and maintaining coincidence of said mark and images during treatment.

18. A method according to claim 17 in which said treatment beam and said cursor mark which indicates the focal point of said treatment beam are displaced by moving a focusing means of said treatment beam to bring said mark into coincidence with said images before and during treatment.

19. A method as set forth in claim 17 wherein said treatment is for effecting hyperthermia by causing local heating at the treatment beam focus in said zone.

20. A method as set forth in claim 17 wherein said treatment beam is an ultrasonic beam.

21. A method as set forth in claim 17 wherein said treatment is for causing a therapeutic increase in the temperature of said zone by local heating at the focus of the treatment beam.

22. A method for treating a zone, having at least one reflecting surface for ultrasonic waves and located within a body, by treatment vibrations, said method comprising the steps of:
 (a) locating said zone by generating from a first transducer means having an active surface a first real time scanning ultrasonic beam and scanning and sweeping said zone with said first beam, whereby echoes are formed through reflection of said first beam on said at least one reflecting surface; receiving said echoes upon said active surface; converting said received echoes into electric signals and forming from said signals two dimensional real time images of said zone through at least one plane;
 (b) generating and discharging from a second transducer means, at a focal point thereof which is located in said at least one plane, a focused treatment beam providing said treatment vibrations;
 (c) displacing said focal point of said second transducer means relative to said zone; and displaying and maintaining a cursor mark indicating said focal point within said images of said zone.

23. A method as set forth in claim 22 wherein said treatment is for effecting hyperthermia by causing local heating at the treatment beam focus in said zone.

24. A method as set forth in claim 22 wherein said treatment beam is an ultrasonic beam.

25. A method as set forth in claim 22 wherein said treatment is for causing a therapeutic increase in the temperature of said zone by local heating at the focus of the treatment beam.

26. A method for treatment of a zone within a body of a patient, comprising the steps of:
 (a) providing a focusing surface having a focal point at a distance from said surface; and a first ultrasonic scanning transducer having an axis between said focal point and said surface, said scanning transducer being coupled to said surface and radiating an acoustical signal beam;
 (b) locating said zone by sweeping said signal beam across an angular sector including said zone;
 (c) detecting reflections of said signal beam and displaying said reflections of said signal beam in real time on a visual display having a mark which indicates the position of said focal point;
 (d) positioning said surface to locate said focal point at said zone by bringing said mark into coincidence with displayed reflections from said zone;
 (e) generating from a second treatment transducer a treatment wave focused by said surface upon said zone; and
 (f) coupling said treatment wave through a portion of said body to concentrate treatment wave energy at said zone.

27. A method as set forth in claim 26 wherein said treatment is for effecting hyperthermia by causing local heating at the focal point in said zone.

28. A method as set forth in claim 26 wherein said treatment wave is an ultrasonic wave.

29. A method as set forth in claim 26 wherein said treatment is for causing a therapeutic increase in the temperature of said zone by local heating at the focus of the treatment wave.

30. A method for operating a wave treatment device which treats a target within a living body comprising:
 (a) generating treatment waves from a treatment wave transducer;
 (b) focusing said treatment waves through ultrasound coupling means at a focal spot beyond said coupling means;
 (c) displaying an image of said target by sweeping an ultrasonic scanning beam through said ultrasound coupling means across said target; and displaying a visual indication of the position of said focal spot; and
 (d) displacing said treatment wave transducer to bring said image and said visual indication into coincidence.

31. A method as set forth in claim 30 wherein said treatment is for effecting hyperthermia by causing local heating at the focal spot.

32. A method as set forth in claim 30 wherein said treatment wave is an ultrasonic wave.

33. A method as set forth in claim 30 wherein said target is a zone to be treated.

34. A method as set forth in claim 30 wherein said treatment is for causing a therapeutic increase in the temperature at said focal spot.

35. A method for treating a zone, having reflecting surfaces for ultrasonic waves and located within a body, by an interrupted beam of treatment vibrations generated from a treatment transducer and converging at a focus, said method comprising the steps of:
  (a) locating said zone by generating an echographic ultrasonic beam from an echographic transducer and effecting periodic sweeps of said echographic ultrasonic beam across said zone for scanning said zone with said echographic ultrasonic beam, whereby echoes are formed through reflection of said echographic ultrasonic beam on said reflecting surfaces; receiving echoes from said surfaces; converting the received echoes into electric signals; forming from said signals two dimensional images of the zone through at least one plane in a predetermined area of a display surface; and displaying a visual indication of said focus within said area in a fixed relative position with respect to said area;
  (b) treating said zone by generating treatment beam discharges from said treatment transducer focused on said zone; and
  (c) scanning and sweeping said zone at least between treatment discharges with said echographic beam to produce images of treatment progress.

36. A method as set forth in claim 35 wherein said treatment is for effecting hyperthermia by causing local heating at the treatment beam focus in said zone.

37. A method as set forth in claim 35 wherein said treatment beam discharges are ultrasonic.

38. A method as set forth in claim 37 wherein the step of treating said zone comprises generating groups of treatment beam discharges separated by interruptions during which no treatment beam discharges are generated, each of said groups of treatment beam discharges comprising at least two treatment beam discharges.

39. A method as set forth in claim 35 wherein the step of treating said zone comprises generating groups of treatment beam discharges separated by interruptions during which no treatment beam discharges are generated, each group of treatment beam discharges having a duration during which treatment beams are discharged from said treatment transducer, each of said interruptions having a duration, wherein said duration of each group of treatment beam discharges is longer in time than said duration of each of said interruptions.

40. A method as set forth in claim 35 wherein the step of treating said zone comprises generating groups of treatment beam discharges separated by interruptions during which no treatment beam discharges are generated, each of said groups of treatment beam discharges comprising at least two treatment beam discharges.

41. A method as set forth in claim 35 wherein said treatment is for causing a therapeutic increase in the temperature of said zone by local heating at the focus of the treatment beam.

* * * * *